US005686120A

United States Patent [19]
Mertz et al.

[11] Patent Number: 5,686,120
[45] Date of Patent: Nov. 11, 1997

[54] PRE-MRNA PROCESSING ENHANCER AND METHOD FOR INTRON-INDEPENDENT GENE EXPRESSION

[75] Inventors: Janet E. Mertz; Xuedong Liu, both of Madison, Wis.

[73] Assignee: Wisconsin Alumni Research Foundation, Madison, Wis.

[21] Appl. No.: 447,313

[22] Filed: May 22, 1995

[51] Int. Cl.$^6$ .................................................. C12N 15/00
[52] U.S. Cl. ...................................... 435/320.1; 536/24.1
[58] Field of Search .............................. 435/69.1, 320.1; 536/24.1; 935/22, 44

[56] References Cited

FOREIGN PATENT DOCUMENTS

WO92/08796  5/1992  WIPO ........................... C12N 15/65

OTHER PUBLICATIONS

Kashiwagi et al., Involvement of ribonuclease III in the enhancement of expression of the speF–potE operon, Biochem. Biophys. Res. Commun. 200:591–597, Apr. 15, 1994

Wagner et al., Nucleotide sequence of the thymidine kinase gene, Proc. Nat. Acad. Sci. USA 78: 1441–1445, Mar. 1981.

Prescott and Falck–Pedersen, Sequence elements upstream of the 3' cleavage site confer substrate strength to the adenovirus L1 and L3 polyadenylation sites, Mol. Cell. Biol. 14: 4682–4693, Jul. 1994.

Huang and Gorman, Intervening sequeces increase efficiency of RNA 3' processing and accumulation of cytoplasmic RNA, Nucleic Acids Res. 18: 937–947, 1990.

Sjoberg et al., A significantly improved semliki forest virus expression system based on the translation enhancer segments from the viral capsid gene, Biotechnol. 12: 1127–1131, Nov. 12, 1994.

Buchman, A.R., et al., "Comparision of Intron–Dependent and Intron–Independent Gene Expression," *Mol. Cell. Biol.* 8(10):4395–4405, 1988.

Greenspan, D.S., et al., "Synthesis of Predominantly Unspliced Cytoplasmic RNAs by Chimeric Herpes Simplex Virus Type 1 Thymidine Kinase–Human β–Globin Genes," *Mol. Cell. Biol.* 5(8):1894–1900, 1985.

Legrain, P., et al., "Come Cis–and Trans–Acting Mutants for Splicing Target Pre–mRNA to the Cytoplasm," *Cell* 57:573–583, 1989.

Liu, X., et al., "A 68 kDa Sequence–specific RNA Binding Protein Involved in Processing of Intronless pre–mRNAs," p. 258, abstract presented at RNA Processing Meeting at RNA Society Meeting,May 28, 1994.

McKnight, S.L., "The Nucleotide Sequence and Transcript Map of the Herpes Simplex Virus Thymidine Kinase Gene," *Nucl. Acids Res.* 8(24):5949–5963, 1980.

Ryu, W.–S., "Processing of Transcripts Made From Intron–Containing and Intronless Protein–Coding Genes," pp. iii, iv, 121, 122, 149, 158–162, 229, Ph.D. Thesis submitted Oct., 1989.

Liu, X., "Effects of Intron and Exon Sequence Elements on Intron–dependent and Intron–independent Gene Expression," Ph.D. thesis, catalogued on Nov. 24, 1994.

*Primary Examiner*—James Ketter
*Assistant Examiner*—Irem Yucel
*Attorney, Agent, or Firm*—Quarles & Brady

[57] ABSTRACT

A chimeric RNA molecule comprising at least one pre-mRNA processing element is disclosed. A gene construct comprising a DNA sequence encoding at least one pre-mRNA processing enhancer is also disclosed. A method of enhancing cytoplasmic RNA accumulation is disclosed. This method comprises the step of inserting a DNA sequence encoding the RNA into the vector described and expressing the DNA sequence.

4 Claims, 6 Drawing Sheets

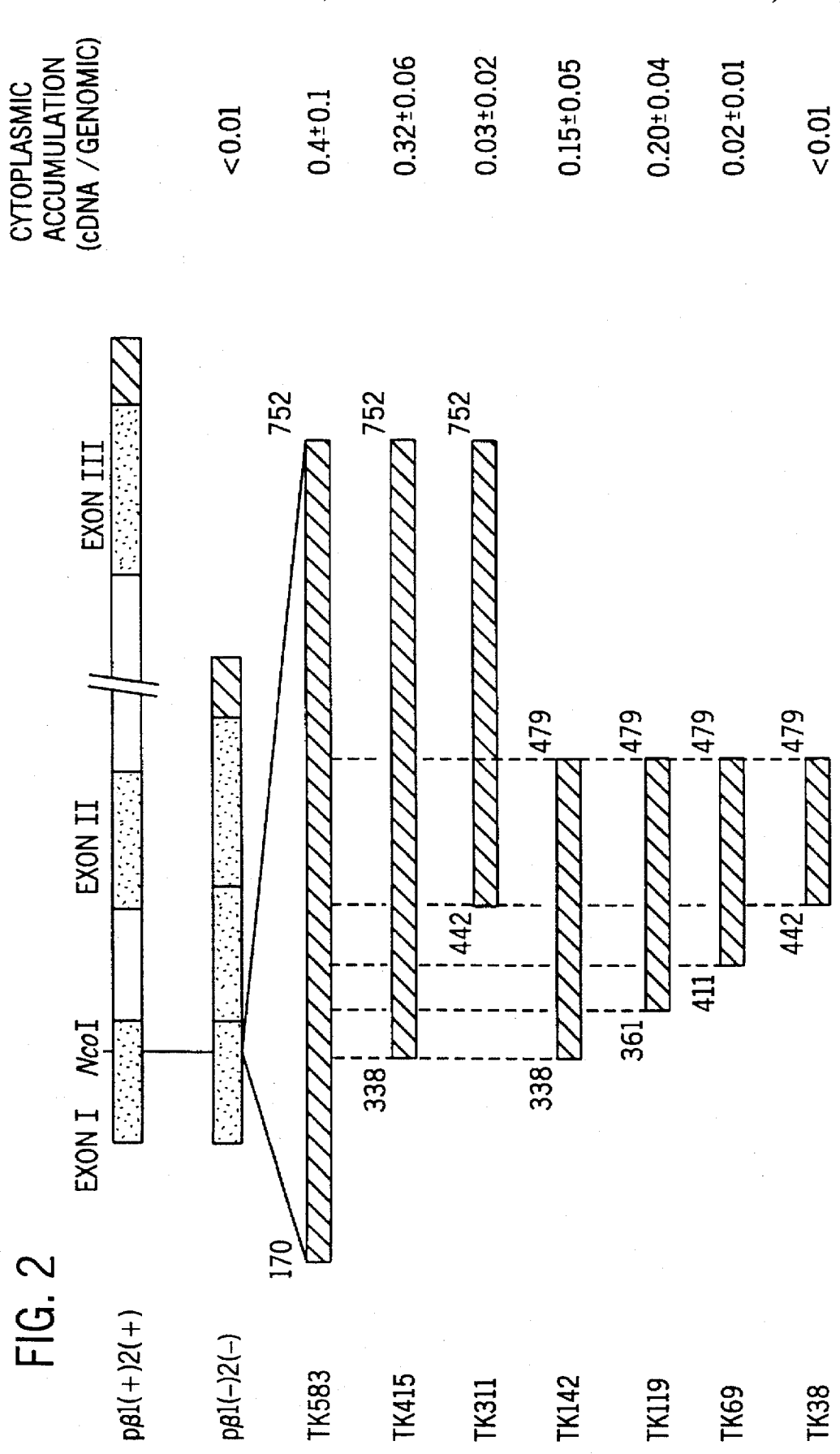

SEQUENCE LISTING ( 1 ) GENERAL INFORMATION:

( i i i ) NUMBER OF SEQUENCES: 12

( 2 ) INFORMATION FOR SEQ ID NO:1:

( i ) SEQUENCE CHARACTERISTICS:
( A ) LENGTH: 119 base pairs ( B ) TYPE: nucleic acid
        ( C ) STRANDEDNESS: double
        ( D ) TOPOLOGY: linear ( i i ) MOLECULE TYPE: DNA (genomic)

( x i ) SEQUENCE DESCRIPTION: SEQ ID NO:1:

GATGACTTAC TGGCAGGTGC TGGGGGCTTC CGAGACAATC GCGAACATCT ACACCACACA         60

ACACCGCCTC GACCAGGGTG AGATATCGGC CGGGGACGCG GCGGTGGTAA TGACAAGCG         119

( 2 ) INFORMATION FOR SEQ ID NO:2:

( i ) SEQUENCE CHARACTERISTICS:
        ( A ) LENGTH: 27 base pairs
        ( B ) TYPE: nucleic acid
        ( C ) STRANDEDNESS: double
        ( D ) TOPOLOGY: linear ( i i ) MOLECULE TYPE: Oligonucleotide ( x i ) SEQUENCE DESCRIPTION: SEQ ID NO:2:

TTAGGCAGAA TCCAGATGCT CAAGGCC                                            27

( 2 ) INFORMATION FOR SEQ ID NO:3:

( i ) SEQUENCE CHARACTERISTICS:
        ( A ) LENGTH: 24 base pairs
        ( B ) TYPE: nucleic acid
        ( C ) STRANDEDNESS: double
        ( D ) TOPOLOGY: linear ( i i ) MOLECULE TYPE: Oligonucleotide ( x i ) SEQUENCE DESCRIPTION: SEQ ID NO:3:

ACATTTGCTT CTGACACAAC TGTG                                               24

( 2 ) INFORMATION FOR SEQ ID NO:4:

( i ) SEQUENCE CHARACTERISTICS:
        ( A ) LENGTH: 12 base pairs
        ( B ) TYPE: nucleic acid
        ( C ) STRANDEDNESS: double
        ( D ) TOPOLOGY: linear ( i i ) MOLECULE TYPE: Oligonucleotide ( x i ) SEQUENCE DESCRIPTION: SEQ ID NO:4:

ATCTACACCA CA                                                            12

( 2 ) INFORMATION FOR SEQ ID NO:5:

( i ) SEQUENCE CHARACTERISTICS:
        ( A ) LENGTH: 13 base pairs
        ( B ) TYPE: nucleic acid
        ( C ) STRANDEDNESS: double
        ( D ) TOPOLOGY: linear ( i i ) MOLECULE TYPE: Oligonucleotide ( x i ) SEQUENCE DESCRIPTION: SEQ ID NO:5:

TAGTAGATCT AGA                                                           13

( 2 ) INFORMATION FOR SEQ ID NO:6:

( i ) SEQUENCE CHARACTERISTICS:
        ( A ) LENGTH: 34 base pairs
        ( B ) TYPE: nucleic acid
        ( C ) STRANDEDNESS: single
        ( D ) TOPOLOGY: linear (i i) MOLECULE TYPE: Other Nucleic Acid (x i) SEQUENCE DESCRIPTION: SEQ ID NO:6:

TCGCGAACAT CTACACCACA CAACACCGCC TCGA                                    34

(2) INFORMATION FOR SEQ ID NO:7:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (i i) MOLECULE TYPE: Other Nucleic Acid (x i) SEQUENCE DESCRIPTION: SEQ ID NO:7:

TCGCGAACTA GTAGATCTAG AAACACCGCC TCGA                                    34

(2) INFORMATION FOR SEQ ID NO:8:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (i i) MOLECULE TYPE: Other Nucleic Acid (x i) SEQUENCE DESCRIPTION: SEQ ID NO:8:

TCGCGAACAT CTACACCAGA TCTCACCGCC TCGA                                    34

(2) INFORMATION FOR SEQ ID NO:9:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (i i) MOLECULE TYPE: Other Nucleic Acid (x i) SEQUENCE DESCRIPTION: SEQ ID NO:9:

TCGCGAACAT CTACACCACA CAAAGATCTC TCGA                                    34

(2) INFORMATION FOR SEQ ID NO:10:

(i) SEQUENCE CHARACTERISTICS:
        (A) LENGTH: 119 base pairs
        (B) TYPE: nucleic acid
        (C) STRANDEDNESS: double
        (D) TOPOLOGY: linear (i i) MOLECULE TYPE: Other Nucleic Acid (x i) SEQUENCE DESCRIPTION: SEQ ID NO:10:

GATGACTTAC TGGCAGGTGC TGGGGCTTC CGAGACAATC GCGAACTAGT AGATCTAGAA          60

ACACCGCCTC GAGCAGGATG AGATATCGGC CGGGGACGCG GCGGTGGTAA TGACAAGCG        119

(2) INFORMATION FOR SEQ ID NO:11:

(i) SEQUENCE CHARACTERISTICS:
        (A) LENGTH: 119 base pairs
        (B) TYPE: nucleic acid
        (C) STRANDEDNESS: double
        (D) TOPOLOGY: linear (i i) MOLECULE TYPE: Other Nucleic Acid ( x i ) SEQUENCE DESCRIPTION: SEQ ID NO:11:

GATGACTTAC TGGCAGGTGC TGGGGGCTTC CGAGACAATC GCGAACATCT ACACCAGATC　　60

TCACCGCCTC GAGCAGGATG AGATATCGGC CGGGGACGCG GCGGTGGTAA TGACAAGCG　　119

( 2 ) INFORMATION FOR SEQ ID NO:12:

( i ) SEQUENCE CHARACTERISTICS:
        ( A ) LENGTH: 119 base pairs
        ( B ) TYPE: nucleic acid
        ( C ) STRANDEDNESS: double
        ( D ) TOPOLOGY: linear ( i i ) MOLECULE TYPE: Other Nucleic Acid ( x i ) SEQUENCE DESCRIPTION: SEQ ID NO:12:

GATGACTTAC TGGCAGGTGC TGGGGGCTTC CGAGACAATC GCGAACATCT ACACCACACA　　60

AAGATCTCTC GAGCAGGATG AGATATCGGC CGGGGACGCG GCGGTGGTAA TGACAAGCG　　119

PRE-MRNA PROCESSING ENHANCER AND METHOD FOR INTRON-INDEPENDENT GENE EXPRESSION

FIELD OF THE INVENTION

In general, the field of the present invention is methods of intron-independent gene expression. Specifically the field of the present invention is use of pre-mRNA processing enhancers to enhance cytoplasmic accumulation of intronless RNA molecules.

BACKGROUND

Formation of mature mRNAs in higher eukaryotes requires that several processing steps occur in the nucleus prior to transport of the mRNA to the cytoplasm. For intron-containing transcripts, these steps include 5'-cap formation, methylation, 3'-end cleavage and polyadenylation, and splicing. Intronless transcripts do not undergo splicing but, in most cases, still need to undergo these other steps in pre-mRNA processing. Much information has been obtained concerning the biochemistry and machinery involved in these nuclear processing events (see Green, *Annu. Rev. Cell. Biol.* 7:559–599, 1991, for review). Nevertheless, the relationship of these events to nuclear export and cytoplasmic accumulation remains poorly understood.

The first evidence linking splicing and the accumulation of mRNA in the cytoplasm came from studies with SV40 (Gruss, et al., *Proc. Natl. Acad. Sci. USA* 76:4317–4321, 1979). Cells transfected with SV40 mutants lacking an excisable intron in the late region of the viral genome were found to synthesize late transcripts, but not to accumulate late SV40 mRNA in the cytoplasm. The requirement of an intron for efficient cytoplasmic accumulation of mRNA (i.e., intron-dependent gene expression) has been subsequently demonstrated for many other genes as well, including those encoding β-globin (Hamer and Leder, *Cell* 17:737–747, 1979; Buchman and Berg, *Mol. Cell. Biol.* 8:4395–4405, 1988; Ryu, *Processing of transcripts made from intron-containing and intronless protein-coding genes*, Ph.D. Thesis, University of Wisconsin-Madison, Madison, Wis., 1989; Collis, et al., *EMBO. J.* 9:233–240, 1990), ribosomal protein L32 (Chung and Perry, *Mol. Cell. Biol.* 9:2075–2082, 1989), purine nucleoside phosphorylase (PNP) (Jonsson, et al., *Nucleic Acids Res.* 20:3191–3198, 1992), immunoglobulin µ (Neuberger and Williams, *Nucleic Acids Res.* 16:6713–6724, 1988), mouse thymidylate synthase (Deng, et al., *Mol. Cell. Biol.* 9:4079–4082, 1989), mouse DHFR (Gasser, et al., *Proc. Natl. Acad. Sci. USA* 79:6522–6526, 1982), plant alcohol dehydrogenase-1 (Callis, et al., *Genes & Dev.* 1:1183–1200, 1987), and triosephosphate isomerase (TPI) (Nesic, et al., *Mol. Cell. Biol.* 13:3359–3369, 1993). It has been proposed that the presence of introns can protect pre-mRNAs from degradation in the nucleus (Hamer and Leder, 1979, supra; Buchman and Berg, 1988, supra; Ryu and Mertz, *J. Virol.* 63:4386–4394, 1989), facilitate polyadenylation (Collis, et. al., 1990, supra; Huang and Gorman, *Nucleic Acids Res.* 18:937–947, 1990; Niwa, et al., *Genes & Dev.* 4:1552–1559, 1990; Pandey, et al., *Nucleic Acids Res.* 18:3161–3170, 1990; Nesic, et al., 1993, supra; Ryu, et al., manuscript in preparation, 1995), facilitate excision of an adjacent intron (Ryu, 1989, supra; Nesic and Maquat, *Genes & Dev.* 8:363–375, 1994), and target mRNAs for export to the cytoplasm (Hamer and Leder, 1979, supra; Buchman and Berg, 1988, supra; Chang and Sharp, *Cell* 59:789–795, 1989; Legrain and Rosbash, *Cell* 57:573–583, 1989; Ryu and Mertz, 1989, supra).

Because of this intron requirement, the complementary DNA (cDNA) version of most genes is expressed quite poorly in mammalian cells. This poor expression cannot be overcome by use of a strong transcriptional promoter because the defects in the expression of intron-dependent genes are post-transcriptional in nature. Genomic versions of genes frequently cannot be used because (i) they have yet to be isolated, or (ii) they are too large to incorporate into useful expression vectors.

Many workers have tried to improve the expression of the cDNA versions of genes by inserting an intron back into either the protein-coding region of the gene or its 3' untranslated region. This approach is frequently unsuccessful as well because many introns (i) cannot enable efficient processing and cytoplasmic accumulation of pre-mRNAs (e.g., Ryu, 1989, supra; Nesic, et al., 1993, supra; Jonsson, et al., 1992, supra) or (ii) lead to the production of cryptically spliced mRNAs which encode incorrect proteins (Huang, et al., *Mol. Cell. Biol.* 10:1805–1810, 1990; Evans, et al., *Gene* 84:135–142, 1989).

Interestingly, although most pre-mRNAs in higher eukaryotes require introns for efficient mRNA biogenesis, this intron requirement is not universal. The genes encoding herpes simplex virus type 1 thymidine kinase (HSV-TK) (McKnight, *Nucleic Acids Res.* 8:5949–5964, 1980), histone proteins (Kedes, *Annu. Rev. Biochem.* 48:837–870, 1978), interferon-α (Nagata, et al., *Nature* 287:401–408, 1980), β-adrenergic receptor (Koilka, et al., *Nature* 329:75–79, 1987), and c-jun (Hattori, et al., *Proc. Natl. Acad. Sci. USA* 9148–9152, 1988) are among those genes discovered to be naturally intronless yet expressed at functional levels in higher eukaryotes.

To begin to understand the mechanism of intron-independent mRNA biogenesis, Greenspan and Weissman (*Mol. Cell. Biol.* 5:1894–1900, 1985), Buchman and Berg (1988, supra), and Ryu (1989, supra) constructed plasmids in which an intron plus some adjacent exon sequence from an intron-requiring β-globin gene was placed 3' of the intronless sequence that encodes HSV-TK. Greenspan and Weissman (1985, supra) found that much of the resulting chimeric TK-globin RNA was polyadenylated and transported to the cytoplasm without intron excision. All three laboratories showed that the chimeric RNAs efficiently accumulated in mammalian cells regardless of whether an intron was present in the primary transcript.

One hypothesis to explain these data is that transcripts synthesized from β-globin and other intron-dependent genes contain negative, cis-acting RNA sequence elements that prevent them from being properly processed and/or transported in the absence of introns; transcripts synthesized from intron-independent genes lack these negative elements and, thus, do not require introns for proper processing and transport. During the past decade, considerable data has accumulated in the literature in support of this hypothesis. For example, Legrain and Rosbash (1989, supra) found that mutations in splicing signals that converted an intron-containing gene into an intronless one led to efficient cytoplasmic accumulation of the intronless transcripts in yeast. Thus, they hypothesized that intronless transcripts are transported to the cytoplasm by default pathways.

An alternative, non-mutually exclusive hypothesis is that transcripts synthesized from intron-independent genes contain positive, cis-acting RNA sequence elements that enable them to be processed and transported regardless of whether or not introns are present. Greenspan and Weissman (1985, supra) and Buchman and Berg (1988, supra) found that various non-overlapping regions of the HSV-TK gene accumulate in cells in the absence of intron excision. Thus, HSV-TK transcripts are processed and transported to the cytoplasm regardless of introns because they either (i) lack a negative cis-acting element, or (ii) contain multiple, positive, cis-acting elements. Their data could not distinguish between these two hypotheses and was more supportive of the first hypothesis.

We show below that positive, cis-acting elements, called pre-mRNA processing enhancers (PPEs), exist. These sequence elements are capable of enabling intron-independent gene expression. Thus, their incorporation into genes provides an alternative approach to inserting introns for obtaining efficient processing and cytoplasmic accumulation of RNAs in higher eukaryotes.

SUMMARY OF THE INVENTION

To test whether transcripts of the HSV-TK gene actually do contain positive, cis-acting RNA sequence elements that enable intron-independent pre-mRNA processing and transport in higher eukaryotes, we examined processing and transport in mammalian cells of transcripts synthesized from an intronless variant of the human β-globin gene containing insertions of various sequences from the HSV-TK gene. We found that a 119-nt sequence (SEQ ID NO:1) contained within the transcribed region of the HSV-TK gene can enable efficient cytoplasmic accumulation of β-globin transcripts in the absence of splicing. Furthermore, we also found that hnRNP L, an abundant, 68 kDa cellular protein of previously unknown function, associates sequence-specifically with this pre-mRNA processing enhancer (PPE), but not with a mutant variant of it defective in rescuing the cytoplasmic accumulation of intronless human β-globin transcripts. The intronless cellular gene c-jun was also found to contain sequences that enable intron-independent pre-mRNA processing and transport. Thus, intron-independent pre-mRNA processing and transport probably involves sequence-specific RNA-protein interactions between PPEs and appropriate cellular factors such as hnRNP L.

In one embodiment, the present invention is a chimeric RNA molecule containing one or more pre-mRNA processing enhancers. The chimeric RNA molecule comprises a first and a second RNA sequence. The first RNA sequence contains a pre-mRNA processing enhancer that is not natively connected to the second RNA sequence.

Preferably, the RNA comprises a 5' untranslated region, a 3' untranslated region, and a protein-encoding region. Inserted into the 5' untranslated region or 3' untranslated region is at least one PPE sequence. The PPE sequence is not natively connected to the protein-encoding sequence.

Preferably, the chimeric RNA molecule comprises two or more PPE sequences.

In another embodiment, the present invention is an isolated population of DNA molecules containing one or more pre-mRNA processing enhancers (PPEs). These molecules are intended to be used as "cassettes" that would be inserted into genetic constructs to enhance the expression of intronless RNA molecules that would otherwise accumulate at an unsatisfactory level. For example, the cassette may be placed 5' or "upstream" of a intronless version of a protein-encoding sequence. Such a sequence is typically created during cDNA cloning. Preferably, the PPE would be placed 3' or "downstream" of an operable transcriptional promoter sequence.

In another embodiment, the present invention is a gene construct comprising at least one (preferably two) pre-mRNA processing enhancers downstream of a transcriptional promoter and 5' of a restriction endonuclease site and signals for transcription termination and 3'-end formation (e.g., polyadenylation signal, ribozyme cleavage signal). This restriction endonuclease site is preferably unique in the vector and designed to accommodate a protein-encoding sequence. Such a construct would be useful to allow one to place an RNA-encoding sequence of choice downstream of a PPE.

In another embodiment, the present invention is a method to enhance cytoplasmic accumulation of intronless RNAs comprising the steps of inserting an RNA-encoding DNA sequence into the vector described above and expressing the RNA sequence (e.g., to enable efficient cytoplasmic accumulation of "anti-sense" RNAs).

In another embodiment, the present invention is a kit for enhancing the cytoplasmic accumulation of intronless RNAs comprising the vector described above.

In another embodiment, the present invention is a gene construct comprising at least one pre-mRNA processing enhancer operably connected to a DNA sequence intended to be expressed as an RNA molecule. The gene construct is designed so that the PPE is expressed within the 5' untranslated region of the RNA expression product.

It is an object of the present invention to provide a DNA sequence capable of being inserted into a genetic construct so that the DNA sequence is expressed as part of the 5' untranslated region or 3' untranslated region of an RNA molecule. Thus, the DNA sequence will enable one to form an mRNA product with enhanced cytoplasmic accumulation.

It is another object of the present invention to provide SEQ ID NO:1, an example of a PPE.

It is another object of the present invention to provide a gene construct suitable for enhancing the cytoplasmic accumulation of RNA molecules.

Other objects, features and advantages of the present invention will become apparent after review of the specification, claims and figures.

DESCRIPTION OF THE DRAWINGS

FIG. 1A shows the structures of plasmids containing an insertion of the transcribed region of the HSV-TK gene into the 5'-untranslated region of the human β-globin gene and a summary of the data obtained with these plasmids. (Noteworthy is our finding that insertion of the HSV-TK sequences into the β-globin gene increases cytoplasmic accumulation of intronless transcripts at least 45-fold from <0.01 to 0.45.) FIG. 1B is a schematic diagram of the human β-globin probe used in the S1 nuclease mapping analysis and the size of the DNA fragments resulting from protection by hybridization with the corresponding RNA. FIG. 1C is a schematic diagram of the cellular β-actin probe used as an internal control in the S1 nuclease mapping experiment.

FIG. 2 is a diagram of the structure of various plasmids containing different portions of the HSV-TK gene inserted into the NcoI site of human β-globin gene and the data obtained with these plasmids. The NcoI site is situated in the 5' untranslated region of this gene. The inserted HSV-TK sequences are relative to the transcription initiation site in the HSV-TK gene (McKnight, et al., *Cell* 25:385-398, 1981). The data in the column on the right are the amount of β-globin-like RNA accumulated in the cytoplasm of cells transfected with the plasmid containing the cDNA version of the indicated gene relative to the amount accumulated in cells transfected in parallel with the plasmid containing the corresponding genomic version of this gene. To determine the effect of the insertion of a given TK sequence on intronless globin RNA accumulation, the numbers in the right column should be compared to each other. For example, insertion of the TK119 sequence into the NcoI site of the cDNA version of the human β-globin gene increases cytoplasmic accumulation of β-globin RNA at least 20-fold (i.e., 0.20 vs. less than 0.01).

DESCRIPTION OF THE INVENTION

1. In General

One problem frequently encountered in trying to efficiently express genes in mammalian cells in culture or animals is very poor expression of the cDNA version of the gene of interest. The cDNA version of an mRNA placed downstream of a transcriptional promoter is one example of an "intronless gene." We refer to a transcript or pre-mRNA synthesized from such an intronless gene as an "intronless" transcript or pre-mRNA. After processing and transport to the cytoplasm, these RNAs are referred to as "intronless" RNAs or mRNAs.

We have identified novel sequence elements, called pre-mRNA processing enhancers or "PPEs", that enable efficient cytoplasmic accumulation of intronless RNAs in the absence of splicing. The inclusion of PPEs in expression vectors will enable one to readily achieve efficient expression of intron-dependent genes in the absence of splicing for use in (i) gene therapy, (ii) the manufacture of proteins, and (iii) basic and applied research. For example, the inclusion of a PPE in an expression vector would enable one to express an mRNA encoding a therapeutic protein in a gene therapy application where expression of a sufficient amount of the therapeutic protein is vital to the success of the treatment.

The present invention involves the use of PPEs in enhancing cytoplasmic accumulation of mRNAs. In one embodiment, the present invention is an mRNA molecule comprising a first and a second RNA sequence. The first RNA sequence comprises at least one PPE. The PPE sequence is not natively connected to the second RNA sequence.

Preferably, the chimeric RNA comprises a 5' untranslated region, a 3' untranslated region, and a protein-encoding sequence. The chimeric RNA comprises at least one PPE within the 5' untranslated region or the 3' untranslated region of the mRNA molecule. The PPE is not natively associated with the protein-encoding sequence or with any other part of the 5' untranslated region or the 3' untranslated region containing the PPE. Most preferably, the PPE is present in two copies.

As described more fully below, the present invention is also a gene construct designed to enhance cytoplasmic accumulation of intronless RNAs or mRNAs and a method for enhancing cytoplasmic accumulation of an intronless RNA or mRNA that utilizes this gene construct.

In another embodiment, the present invention is a preparation of DNA molecules comprising at least one PPE. These molecules would act as a "cassette" to be inserted into a DNA construct 5' of an RNA-encoding sequence. Preferably, the PPE would be placed downstream from a functional promoter.

2. Suitable PPEs

Figure 3:
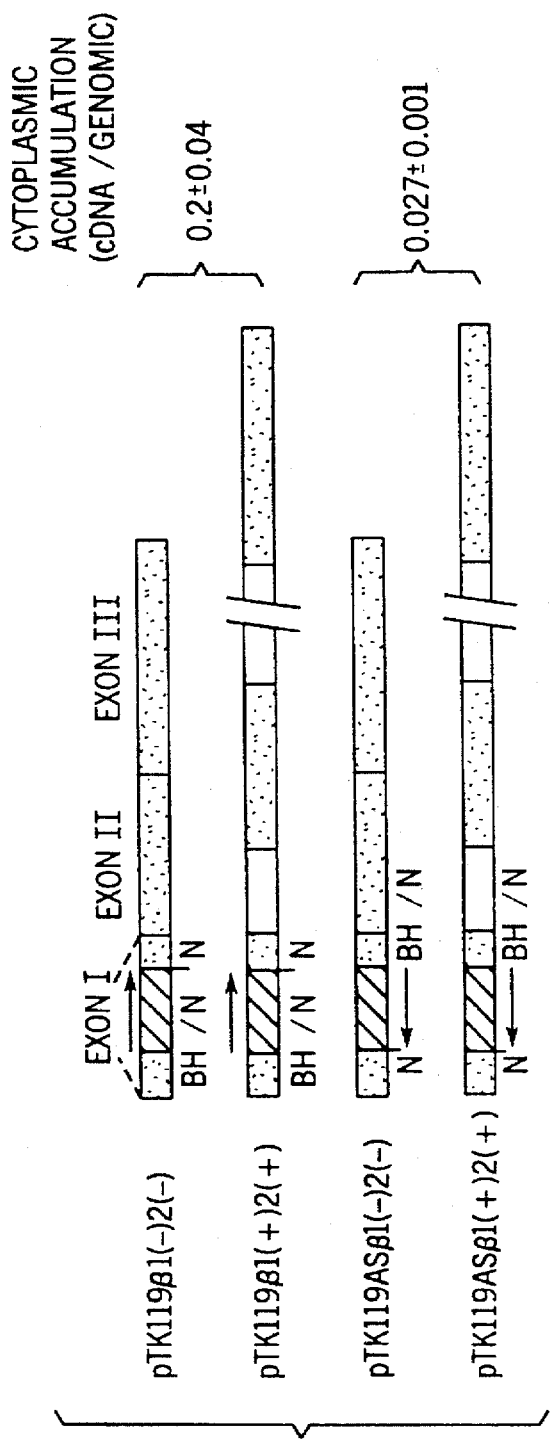
FIG. 3 is a diagram of the structures of plasmids containing an insertion of the HSV-TK element in the sense vs. anti-sense orientation.
Figure 4:
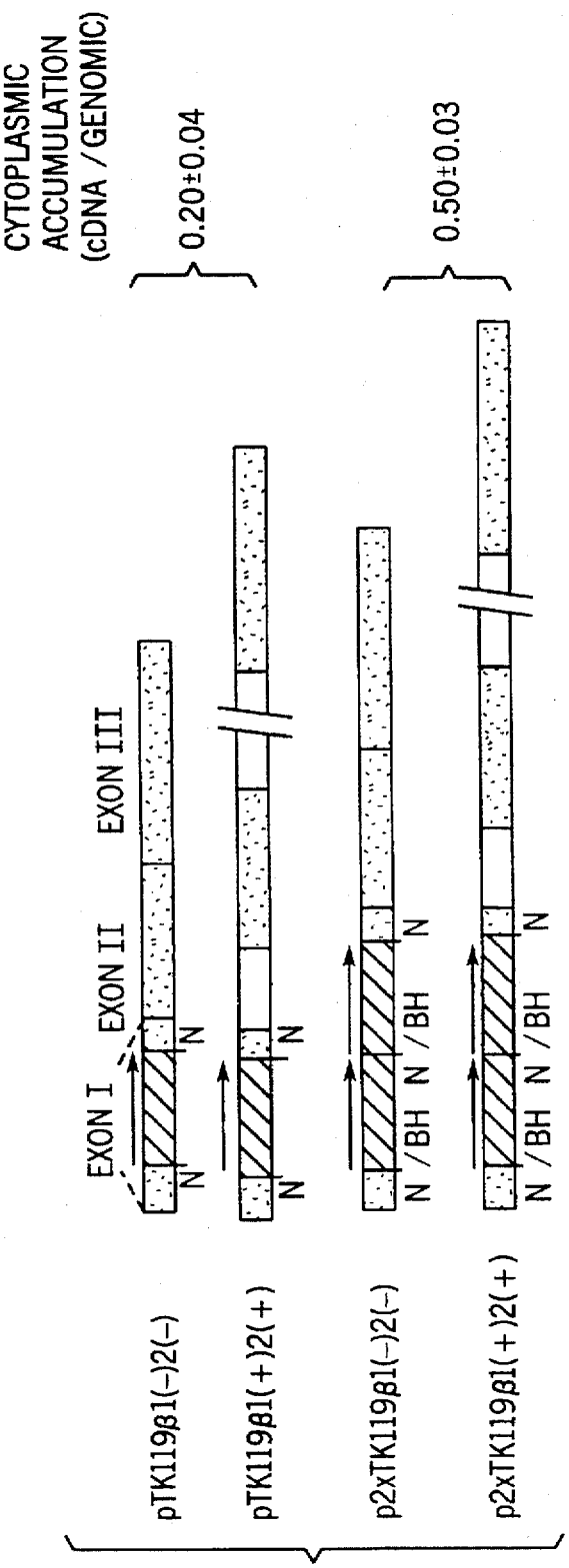
FIG. 4 is a diagram of plasmids containing tandem copies of the HSV-TK nt 361-to-479 and the data obtained with these plasmids.

In accordance with the present invention, we have demonstrated the presence and isolation of a PPE sequence in at least two different genes. First, the examples below disclose that the transcribed region of the naturally intronless HSV-TK gene contains at least one positive, cis-acting sequence element that can enable the proper processing and transport of transcripts synthesized from intronless variants of intron-dependent β-globin genes. We have: (i) localized to a 119-bp region a sequence that can mediate this effect (SEQ ID NO:1, FIG. 2), (ii) shown that this novel sequence element truly enables cytoplasmic accumulation of mRNAs in the absence of splicing (Liu and Mertz, *Genes & Dev.*, in press), (iii) provided evidence that this sequence functions at the RNA level (FIGS. 3 and 6), (iv) demonstrated that the sequence functions in an orientation-dependent manner (FIG. 3), and (v) shown that this element functions more efficiently when present in more than one copy (FIG. 4). We name sequence elements with this novel set of properties PPEs for pre-mRNA processing enhancers.

While SEQ ID NO:1 is a preferred PPE of the present invention, we envision that modifications of SEQ ID NO:1 are also suitable PPEs. It is well known in the art of molecular biology that minor nucleotide changes, additions or deletions may result in no change in the functional nature of the nucleotide sequence. For example, changes in nucleotide 338 (G→A) and 333 (C→G) were tested and did not alter activity of this element. Any nucleotide change or addition that retains at least 25% of the PPE activity of SEQ ID NO:1 is a suitable PPE of the present invention.

Figure 5:
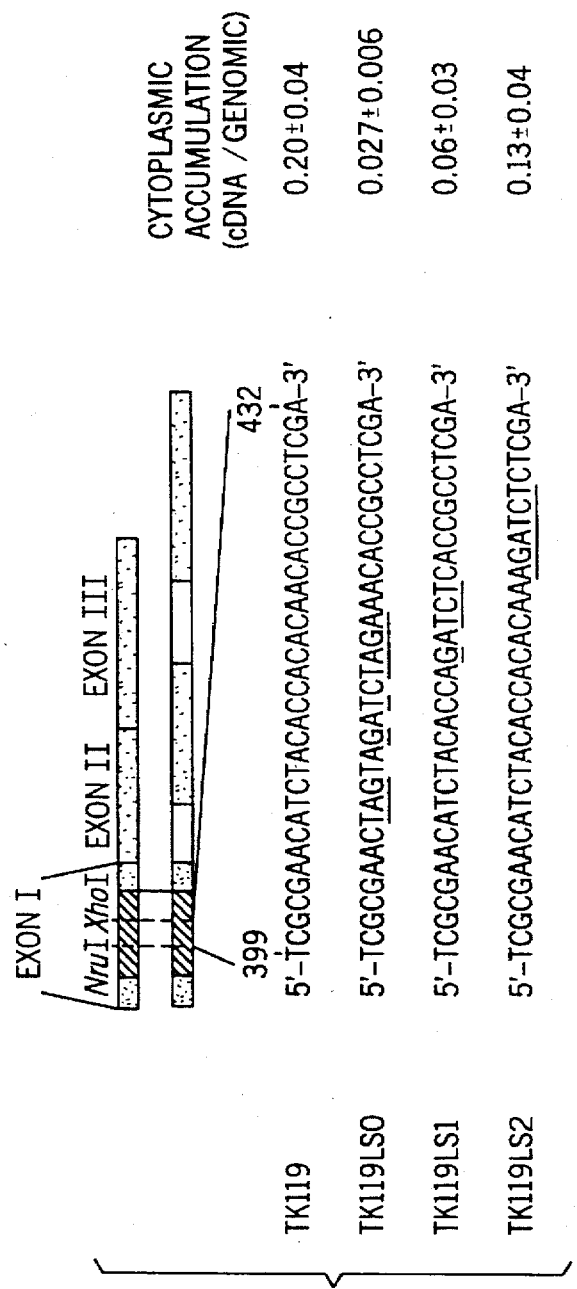
FIG. 5 is a diagram of mutations in the HSV-TK PPE and the abilities of these variants to enable intron-independent gene expression (SEQ ID NOS. 6-9).

For example, FIG. 5 demonstrates some alterations made to the original 119 bp PPE. The sequence alterations present in TK119LSO inactivate this element as a PPE. On the other hand, the sequence alterations present in TK119LS2 enable this sequence to function as a PPE at approximately 65% the level of TK119. Thus, it is still a suitable, though less-than-optional, PPE. Similarly, some deletions, insertions, or substitution mutations in the sequence would probably result in a suitable PPE. TK119LS1 is also a suitable PPE at approximately 30% of the activity of TK119.

Figure 7:
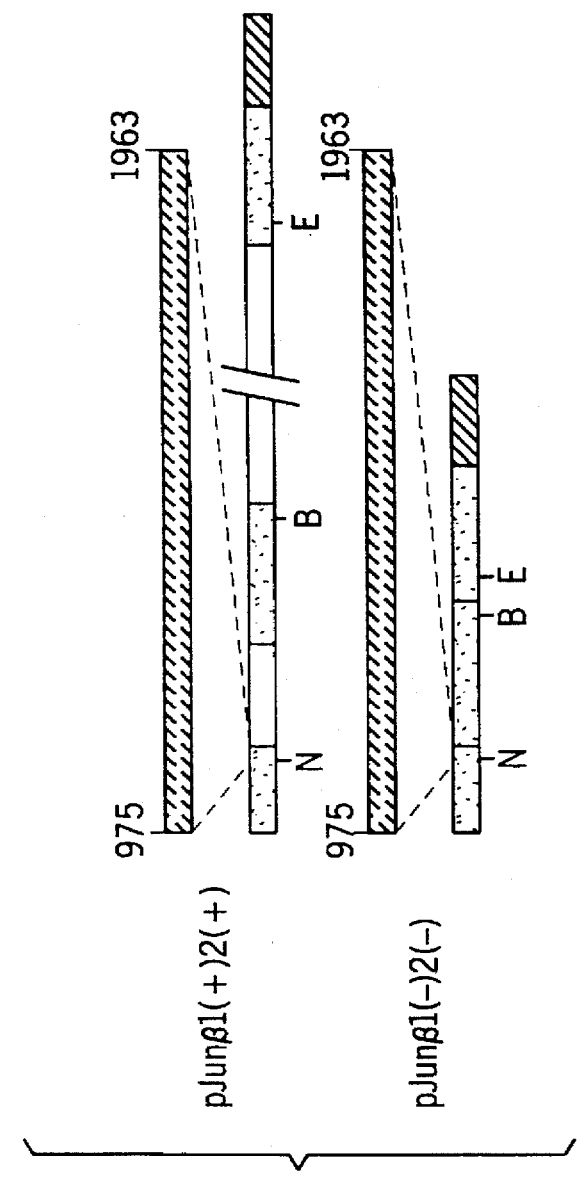
FIG. 7 describes the structures of plasmids containing an insertion of part of the coding region of the c-jun gene into the 5' untranslated region of the human β-globin gene and a summary of the data obtained with these plasmids.

Second, we also show that sequences contained within the naturally intronless cellular gene c-jun can also provide this function (FIG. 7). Thus, at least some cellular genes also contain PPEs and more than one sequence can function as a PPE.

A PPE of the present invention is isolated from the majority of the surrounding gene. Therefore, a 300 bp or larger naturally occurring nucleotide segment containing a single PPE is not a PPE of the present invention. Preferably, a single PPE is localized to a nucleotide sequence less than 200 bp, most preferably less than 140 bp. A PPE must (1) be localized to a nucleotide length of less than 300 bp, (2) function in an orientation-dependent manner, (3) function more efficiently when present in more than one copy, and (4) enhance the cytoplasmic accumulation of an intronless (i.e., cDNA) version of an intron-dependent transcript by at least 2-fold, preferably by at least 5-fold (20-fold or more for β-globin).

Insertion of most of the transcribed region of the HSV-TK gene can, in large part, relieve the requirement for an intron for efficient cytoplasmic accumulation of intronless human β-globin transcripts (Ryu, 1989, supra; FIG. 1). Our deletion mapping data (FIG. 2) indicated that an element contained within nt 361-to-479 (relative to the transcription initiation site) of the HSV-TK gene can largely provide this function. Greenspan and Weissman (1985, supra) and Buchman and Berg (1988, supra) had noted previously that non-overlapping sequences transcribed from the HSV-TK gene can accumulate in mammalian cells in the absence of intron excision. The simplest interpretation of their data was that intronless HSV-TK transcripts lacked negative, cis-acting sequence elements that prevent nuclear export in the absence of splicing. In view of the findings presented here, we now reinterpret their data to indicate, instead, that the HSV-TK gene probably contains at least two PPEs. Consistent with this conclusion are our observations that (i) the HSV-TK PPE we mapped here functions with approximately one-half the efficiency that the full-length HSV-TK gene does (FIG. 1 vs. FIG. 2), and (ii) insertion of two copies of this PPE results in a two-fold increase in the cytoplasmic accumulation of intronless transcripts (FIG. 3). Thus, we hypothesize that multiple copies of PPEs may act in a cooperative or additive manner to enhance the efficiency of processing and nuclear export of pre-mRNAs.

In accordance with the present invention, one may wish to isolate a PPE sequence from an intronless gene other than c-jun or HSV-TK. One would first examine the transcribed region of the selected gene, as we have done below with the HSV-TK gene. Deletion analysis as demonstrated below will enable one to find the appropriate PPE sequence. As described above, the PPE must be isolated from the surrounding gene sequence. A sequence is a suitable PPE sequence if the sequence (1) enhances cytoplasmic accumulation of an intronless transcript by at least 2-fold, (2) functions more efficiently when present in more than one copy, (3) functions in an orientation-dependent manner, and (4) is less than 200 nucleotides in length. Preferably, the PPE enhances cytoplasmic accumulation of an intronless RNA at least 5-fold. Most preferably, the increase is at least 20-fold. We note that if two PPE sequences are present, the combined length may be greater than 200 nucleotides.

3. Suitable RNA Molecules

Pre-mRNAs differ considerably in their requirement for an intron for efficient processing. Introns are absolutely required for expression of the human β-globin (Ryu, 1989, supra; Collis, et al. 1990, supra), rabbit β-globin (Buckman and Berg, 1988, supra), human PNP (Jonsson, et al., 1992, supra) and human TPI (Nesic, et al., 1993, supra) genes. On the other hand, some naturally intron-containing genes [i.e., those encoding polyoma middle T antigen (Treisman, et al., *Nature* 292:595–600, 1981) and cellular thymidine kinase (Gross, et al., *Mol. Cell. Biol.* 7:4576–4581, 1987)] appear to be considerably less dependent upon the presence of introns for processing of their transcripts. Nevertheless, the presence of introns still increases the cytoplasmic accumulation of these latter RNAs at least a few fold.

We envision the present invention to be useful for a variety of mRNAs. Additionally, the present invention is envisioned to be useful in expressing RNA molecules that are not necessarily translated into a protein product. For example, ribozymes and other catalytic RNAs might be usefully expressed by the present invention. Additionally, anti-sense RNAs would also be advantageously expressed.

4. Gene Constructs

In another embodiment, the present invention is a gene construct comprising a DNA sequence encoding at least one copy of a PPE, preferably 5' of a unique restriction endonuclease site. This vector is constructed to accommodate the insertion of an RNA-encoding sequence whose transcript would be accumulated with the addition of a PPE. Typically, the PPE is downstream from a promoter sequence. Preferably, more than one PPE is present in the gene construct. In an especially preferred embodiment, the restriction site is within a polylinker composed of multiple unique restriction endonuclease sites. In an especially preferred embodiment, the construct additionally contains a translation enhancer, such as the enhancer described in U.S. Pat. No. 4,937,190 to Palmenberg, et al. This enhancer would typically be placed downstream of the PPE and upstream of a protein-encoding sequence.

The gene construct of the present invention may be contained within a variety of vectors. Preferential examples are a virus or plasmid vector.

The present invention is also a method of enhancing the cytoplasmic accumulation of RNA molecules. The method comprises the step of insertion of an RNA-encoding sequence into the vector described above and expressing that RNA sequence.

The present invention is also a gene construct comprising at least one copy of a PPE downstream from a functional promoter and upstream from a protein-encoding sequence. Such a gene construct could be useful in many ways. For example, one might make a library of random cDNA sequences within plasmid vectors. These plasmid vectors could contain the PPE sequence in the orientation and location described above. This library would then be suitable for transfection into or transformation of appropriate host cells, such as mammalian cells. Expression of the RNAs and encoded proteins would be at a level sufficient to screen for the desired cDNA.

5. Kits for Enhancing RNA Accumulation

The present invention is also a kit for the enhanced cytoplasmic accumulation of RNAs comprising the restriction endonuclease site-containing vector described above. The kit would typically contain a receptacle containing the restriction endonuclease site-containing vector described above. This vector would be suitable for a kit user to insert an intronless RNA-encoding DNA of interest and, subsequently, obtain efficient cytoplasmic accumulation of the RNA and, where appropriate, translation of the mRNA in a biological system.

The present invention is also a kit for assaying with very high sensitivity for gene expression in single or small numbers of cells. For example, the kit might contain a reporter construct containing a PPE upstream of reporter gene sequences, such as luciferase-encoding or β-galactosidase-encoding sequences. When expressed from a specific inserted transcriptional enhancer/promoter sequence in some cells of a chimeric or transgenic animal, the expressing cells could be detected with improved sensitivity because of the increased abundance of the reporter messages.

EXAMPLES

1. In General

Most pre-mRNAs require an intron for efficient processing in higher eukaryotes. Exceptions to this rule are transcripts synthesized from naturally intronless genes. To test the hypothesis that intron-independent gene expression involves positive, cis-acting RNA sequence elements, we constructed chimeric genes in which various regions of the HSV-TK gene were inserted into an intronless variant of the highly intron-dependent human β-globin gene. Plasmids containing these chimeric genes were transfected into CV-1PD cells. The structures and quantities of the resulting globin-like RNAs were determined by S1 nuclease mapping. A 119-nt sequence element (SEQ ID NO:1) contained within nucleotide residues 361–479 relative to the transcription initiation site of the HSV-TK gene (McKnight, et al., 1981, supra) was found to enable efficient cytoplasmic accumulation of globin-like RNA in the absence of splicing in an orientation-dependent manner. RNA UV-crosslinking assays indicated that a 68 kDa protein present in nuclear extracts of HeLa and COS cells binds specifically to this pre-mRNA processing enhancer (PPE). Analysis of substitution mutants in this PPE indicated that binding of the 68 kDa protein correlates with accumulation of the chimeric RNA in the cytoplasm. A sequence from the transcribed region of the intronless cellular gene c-jun was also found to enable efficient processing of intronless β-globin-like transcripts. Thus, we conclude that: (i) intronless genes contain PPEs, (ii) the 68 kDa protein is a sequence-specific RNA-binding protein, and (iii) intron-independent pre-mRNA processing and transport may involve sequence-specific RNA-protein interactions between PPEs and proteins such as the 68 kDa protein. We propose that PPEs may be of general use for the efficient expression of cDNA versions of intron-dependent genes.

2. Materials and Methods

Cells, Transfections, and Nuclear Extracts

The African green monkey kidney cell line CV-1PD was grown in Dulbecco's modified Eagle's medium (DMEM) supplemented with 5% fetal bovine serum as described previously (Good, et al., *J. Virol.* 62:563–571, 1988). Co-transfections were performed by a modification of the DEAE-dextran/chloroquine procedure essentially as described previously (Liu and Mertz, 1993, supra). The relative transfection efficiencies were determined as described previously (Ryu and Mertz, 1989, supra) by Southern blot analysis of the replicated plasmid DNA present in each sample. HeLa and COS cell nuclear extracts were prepared essentially as described previously (Dignam, et al., *Nucleic Acids Res.* 11:1475–1488, 1983; Terns, "Role of nuclear poly(A) polymerase in the 3'-end processing of precursor messenger RNA," Ph.D. Thesis. Pennsylvania State University, State College, Pennsylvania, 1990).

Recombinant Plasmids

All plasmids were constructed by standard recombinant DNA techniques (Sambrook, et al., *Molecular Cloning: A Laboratory Manual*. Cold Spring Harbor Laboratory Press, Cold Spring Harbor, N.Y., 1989). Plasmid pβ1(+)2(+) contains a genomic version of the human β-globin gene (FIG. 1). Plasmid pβ1(−)2(−) is identical in sequence to pβ1(+)2 (+) except for the precise lack of the two β-globin introns. These plasmids have been described in detail elsewhere (Ryu, 1989, supra; Yu, et al., 1991, supra). Plasmids pTKβ1 (−)2(−) and pTKβ1(+)2(+) contain an insertion of nucleotide residues (nt) 59-to-1238 (relative to the transcription initiation site) of the HSV-TK gene into the NcoI site in the 5'-untranslated region of the plasmids pβ1(−)2(−) and pβ1 (+)2(+), respectively (FIG. 1). These plasmids were constructed by ligation after the HSV-TK sequence to be inserted was generated by PCR-based amplification as described previously (Liu, 1994, supra.). Similar strategies were used in construction of pJunβ1(−)2(−) and pJunβ1(+) 2(+) in which the entire coding region except the terminal codon of c-jun was inserted. A series of TK-deleted, duplicated, and anti-sense-inserted variants of the TK-globin chimeric plasmids (FIGS. 2, 3, and 4; Table 1) were generated likewise (Liu, 1994, supra; Liu and Mertz, 1995, in press, *Genes and Development*). The construction of pTK119Xβ1(−)2(−) and pTK119Xβ1(+)2(+) and the linker-scanning mutant derivatives of these plasmids (FIGS. 5 and 6; Table 1) has also been described in detail elsewhere (Liu, 1994, supra; Liu and Mertz, 1995, supra).

Figure 6:
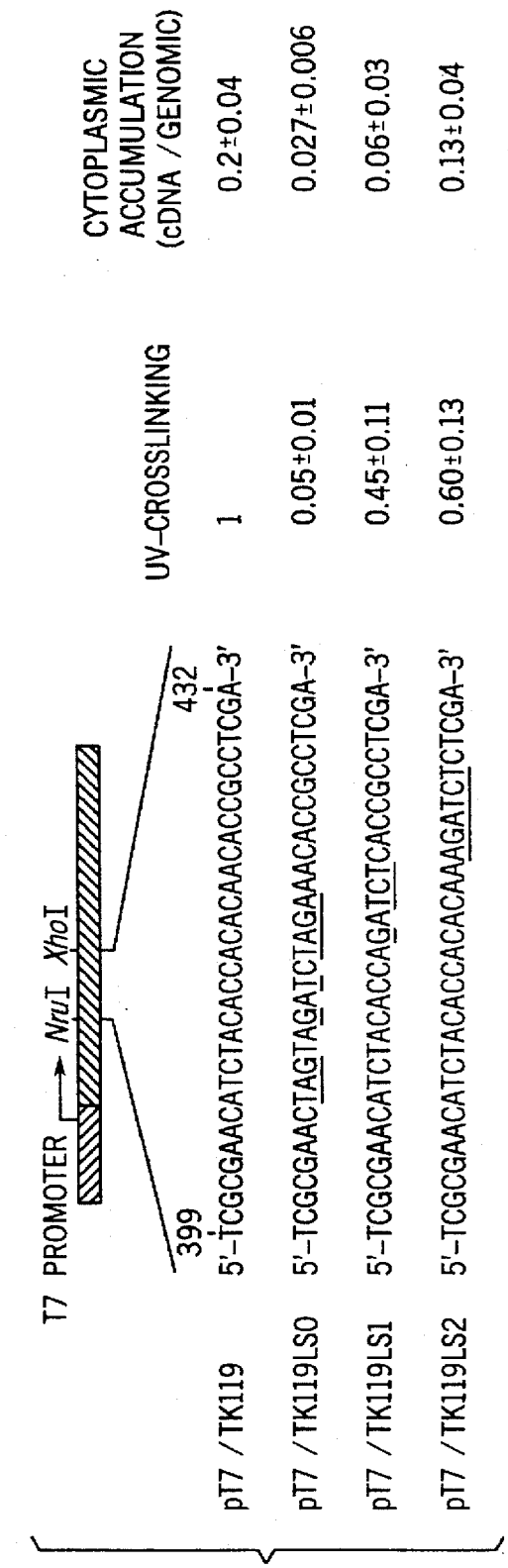
FIG. 6 is a set of schematic diagrams of the transcribed regions of the plasmids with linker-scanning mutations in the PPE used to synthesize the radiolabeled rTK119, rTK119LSO, rTK119LS1, and rTK119LS2 RNAs and the summary of the UV-crosslinking data obtained with these RNAs.

Plasmid pT7/TK119 (FIG. 6) was constructed by insertion of the 119-bp BspHI and NcoI-digested PCR fragment of pTK119β1(−)2(−) into NcoI-digested pGEM5Z(+) in the sense orientation. Plasmids pT7/TK119LS0, pT7/TK119LS1, and pT7/TK119LS2 are identical to pT7/TK119 except for the indicated substitution mutations in the TK sequence element (Table 1; FIG. 6) and some extra globin sequences in the polylinker region 3' of the TK sequences. The RNAs synthesized from these plasmids are designated by "rTK" followed by the length of the RNA and, where appropriate, the mutation name. Plasmids pT7/TK119β1(−)2(−) and pT7/β1(−)2(−) were constructed by insertion of the HindIII- and XbaI-digested PCR fragments of pTK119β1(−)2(−) and pβ1(−)2(−), corresponding to the sequences from the transcription initiation site to 91 bases 3' of the human β-globin polyadenylation signal, into HindIII- and XbaI-digested pGEM2 vector DNA (Promega). Plasmids pJunβ1(+)2(+) and pJunβ1(−)2(−) contain an insertion of nt 975-to-1963 (relative to transcription initiation site) of the c-jun gene (Hattori, et al., 1988, supra) into the NcoI site in the 5'-untranslated region of the plasmids pβ1(+)2(+) and pβ1(−)2(−), respectively; these plasmids were constructed by PCR amplification and insertion as described above.

RNA Purification and S1 Nuclease Mapping Analysis

Nuclear and cytoplasmic RNAs were purified from monkey cells 48 hours after transfection as described previously (Liu and Mertz, 1993, supra). The relative amounts of globin-like RNA accumulated in the nucleus and cytoplasm were determined by quantitative S1 nuclease mapping techniques as described previously (Liu and Mertz, 1993, supra). The probes used in the S1 nuclease mapping analyses are shown in the figures. Cellular β-actin RNA, mapped concurrently, served as an internal control for recovery of the RNA samples and purity of the nuclear RNA (Yu, et al., 1991, supra; Liu and Mertz, 1993, supra). Southern blot analysis of the relative amount of DpnI-resistant, β-globin-encoding plasmid DNA present in each nuclear sample prior to treatment with DNase I was performed as described elsewhere (Ryu, 1989, supra; Liu and Mertz, 1993, supra); it was used to assay for both (i) nuclear contamination of cytoplasmic nucleic acid, and (ii) differences in transfection efficiencies (data not shown). The S1 nuclease-protected DNA fragments were electrophoresed in 8M urea, 5% polyacrylamide gels. Quantitations were performed by scanning with a PhosphorImager (Molecular Dynamics).

RT-PCR, PCR, and DNA Sequencing Analyses

Prior to reverse transcription, each RNA sample for RT-PCR analysis was treated with RNase-free FPLC-pure DNase I (Pharmacia). Each reverse transcription reaction contained 2% of the cytoplasmic RNA harvested from a 100-mm dish of transfected cells, 25 units AMV reverse transcriptase (Boehringer Mannheim), 25 ng 3'-anti-sense primer (5'-TTAGGCAGAATCCAGATGCTCAAGGCC-3', SEQ ID NO:2), 1.25 mM of each of the four dNTPs, and 20 units RNasin (Promega) in a total volume 20 µl. After incubation at 42° C. for 1.5 hours, the reaction mixture was incubated at 95° C. for 10 minutes and quickly chilled on ice to denature the heteroduplexes. Afterward, the PCR reaction was performed in a 50 µl volume containing 10 mM Tris-HCl (pH 8.3), 1.5 mM Mg2Cl, 50 mM KCl, 1.25 mM of each of the four dNTPs, 2.5 unit Taq polymerase, 1 µM each of the 3'-antisense primer and the 5' primer (5'-ACATTTGCTTCTGACACAACTGTG-3', SEQ ID NO:3), and the 20 µl from the reverse transcription reaction. A Perkin-Elmer Cetus thermal cycler was used with denaturation at 94° C. for 1 minute, primer annealing at 55° C. for 1 minute, and extension at 72° C. for 2 minutes for 35 cycles.

UV-crosslinking Assays

The RNA substrates for in vitro studies were synthesized using a commercial T7/SP6 in vitro transcription kit (Promega). The DNAs used as templates for the RNA syntheses were derivatives of pGEM5Z(+) (Promega). One microgram of each template was linearized by digestion with NcoI and transcribed with T7 RNA polymerase at 37° C. for 1 hour in the presence of either [α-$^{32}$P]UTP or [α-$^{32}$P]CTP (3000 Ci/mmol, Amersham). Wild-type and mutant RNA substrates were prepared in parallel to insure their specific activities were similar. After RNA synthesis, the DNA templates were degraded by incubation with RNase-free DNase I (Promega) for 15 minutes at 30° C., and the full-length, radiolabeled transcripts were purified by polyacrylamide gel electrophoresis as described previously (Liu, 1994, supra). For UV-crosslinking assays, 5×10$^4$ cpm of $^{32}$P-labeled RNA was incubated with 5–10 µg HeLa or COS cell nuclear extract, 10 mM KCl, 10% glycerol, 0.2 mM dithiothreitol, and 2 µg yeast tRNA (Boehringer Mannheim) in a total volume of 10 µl at 30° C. for 10 minutes (Gillis and Malter, *J. Biol. Chem.* 266:3172–3177, 1991). Afterward, the reaction mixture was irradiated in a UV-Stratalinker (Stratagene) for 10 minutes on the automatic setting. RNase A was added to a final concentration of 1 mg/ml, and incubation was continued at 37° C. for 15 minutes. After addition of SDS-PAGE sample buffer, each sample was incubated at 100° C. for 4 minutes and electrophoresed in a 15% polyacrylamide gel containing 0.1% SDS. The gels were either dried and autoradiographed overnight at −70° C. or exposed to a PhosphorImager screen and scanned in a PhosphorImager (Molecular Dynamics). Competition UV-crosslinking assays were performed similarly, except for pre-incubation of the nuclear extract with unlabeled RNA prepared following the protocol of Gurevich, et al. (1991).

Figure 1A:
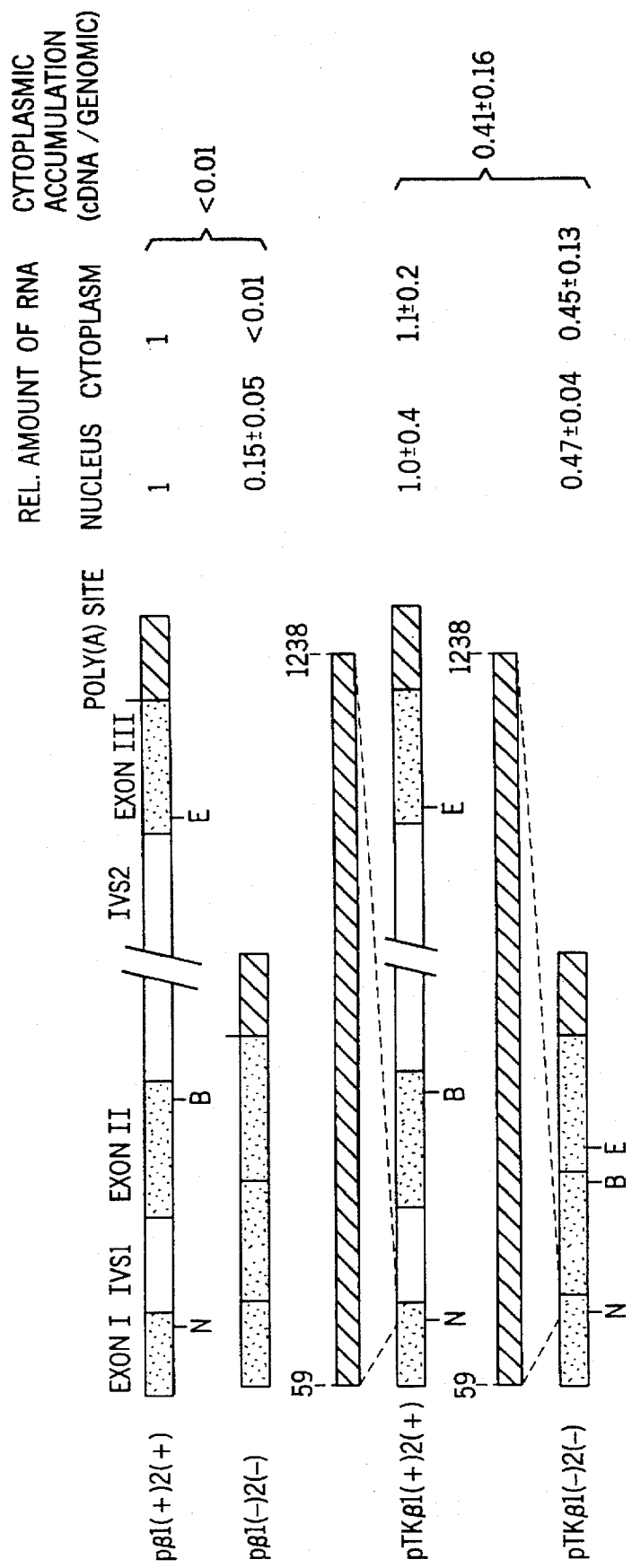
FIGS. 1A-1C demonstrate that the presence of HSV-TK sequences in cis can obviate the intron requirement for processing of human β-globin transcripts.

3. Sequences Contained Within the Transcribed Region of the HSV-TK Gene Enable Efficient Processing of Intronless Human β-globin Transcripts We first constructed pTKβ1(−)2(−) and pTKβ1(+)2(+), plasmids into which the HSV-TK nucleotide residues 59-to-1238 (relative to the transcription initiation site) were inserted in the sense orientation into a complete cDNA and genomic version, respectively, of the human β-globin gene (FIG. 1A). The genomic version of the hybrid gene served as a control for message stability in the cytoplasm. Since the mature mRNAs generated from these plasmids are identical in primary structure, they should have identical half-lives in the cytoplasm unless processing via alternative pathways in the nucleus affects the location or association with ribonuclear proteins in the cytoplasm. Therefore, we assumed that the ratio of TK-globin chimeric RNA accumulated in the cytoplasm of cells transfected in parallel with the cDNA relative to the genomic version of a hybrid gene provides a reasonable indication as to the effectiveness of the HSV-TK sequence in allowing intron-independent gene expression.

These plasmids were co-transfected in parallel into monkey cells along with pRSV-Tori, a plasmid encoding the SV40 large T antigen (Ryu, 1989, supra; Yu, et al., *Nucleic Acids Res.* 19: 7231–7234, 1991). The presence of the latter plasmid results in replication of the test plasmid to high copy number, making structural and quantitative analysis of the accumulated β-globin-like RNAs easy to perform by quantitative S1 nuclease mapping techniques (Ryu, 1989, supra; Yu, et al., 1991, supra; Liu and Mertz, *Nucleic Acids Res.* 21:5256–5263, 1993; Ryu, et al., 1995). As negative and positive controls, we also transfected in parallel the plasmids pβ1(−)2(−) and pβ1(+)2(+) which contain cDNA and genomic versions of the human β-globin gene, respectively. The amounts of cytoplasmic and nuclear globin-like RNA accumulated in cells transfected with each plasmid were determined relative to the amounts accumulated in pβ1(+)2(+)-transfected cells.

FIG. 1 demonstrates that the presence of HSV-TK sequences in cis can obviate the intron requirement for processing of human β-globin transcripts. FIG. 1A shows the structures of plasmids containing an insertion of the transcribed region of the HSV-TK gene into the 5'-untranslated region of the human β-globin gene and a summary of the data obtained with these plasmids. Only the transcribed region of each gene is shown. The remainder of each plasmid is identical in sequence and described in detail elsewhere (Ryu, 1989, supra; Yu, et al., 1991, supra). Referring to FIG. 1A, shaded boxes indicate human β-globin exon sequences; open boxes indicate human β-globin intron sequences; hatched boxes indicate sequences from the transcribed region of the herpes simplex virus type 1 thymidine kinase (HSV-TK) gene; numbers at ends of hatched boxes indicate endpoints of the HSV-TK sequence inserted in nt relative to the HSV-TK gene's transcription initiation site; B indicates BamHI; N indicates NcoI; E indicates EcoRI. The first column on the right indicates the amount of β-globin-like RNA present in the nucleus of cells transfected with each plasmid relative to the amount accumulated in cells transfected in parallel with pβ1(+)2(+). The second column indicates the amount of β-globin-like RNA accumulated in the cytoplasm of these same cells relative to that accumulated in the pβ1(+)2(+)-transfected cells. The last column on the right indicates the amount of β-globin-like RNA present in the cytoplasm of cells transfected with the plasmid containing the cDNA version of the gene relative to the amount accumulated in cells transfected in parallel with the plasmid containing the corresponding genomic version of this gene, with normalization to the relative amounts of (i) cellular β-actin present in the same RNA samples, and (ii) replicated β-globin-encoding plasmid DNA present in the nuclear samples obtained from these cells (data not shown). These data are means ±S.E.M.s from two experiments and were obtained from electrophoretic gels.

Figure 1B:
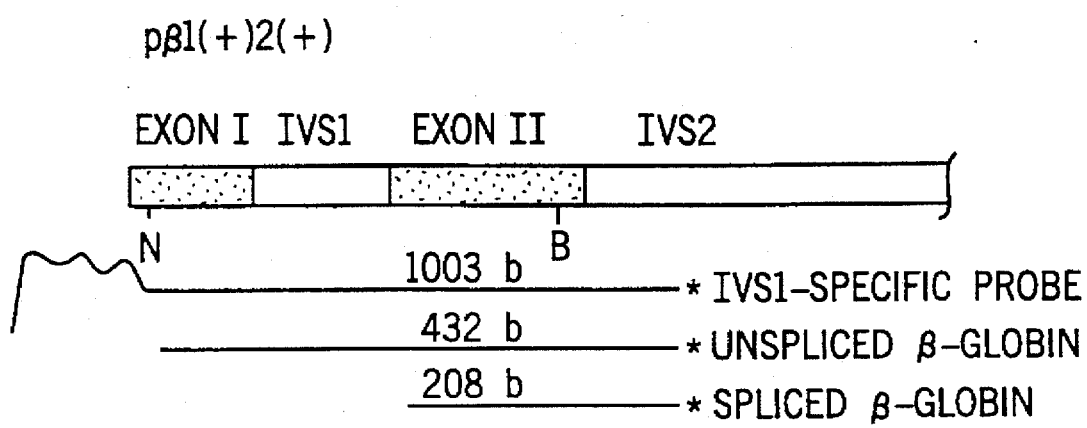

FIG. 1B is a schematic diagram of the human β-globin probe (described previously by Ryu, 1989, supra; Yu, et al., 1991, supra) used in the S1 nuclease mapping analysis and the sized DNA fragments resulting from protection by hybridization with the corresponding RNAs. The human β-globin probe was 5' end-labeled at the BamHI site; the wavy line indicates the discontinuity between the probe and the globin RNA. Abbreviations are as described in panel A.

Figure 1C:
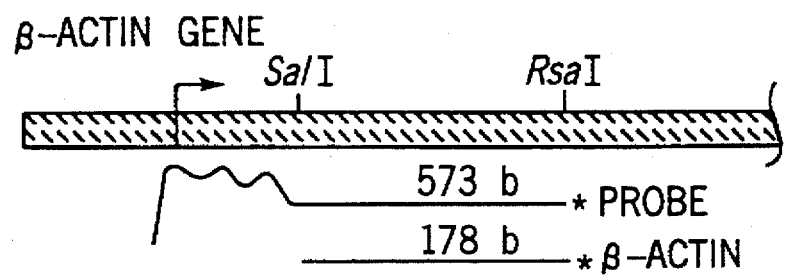

FIG. 1C is a schematic diagram of the cellular β-actin probe, described previously (Ryu, 1989, supra; Yu, et al., 1991, supra), used as an internal control in the S1 nuclease mapping experiment. The actin probe was 5' end-labeled at the RsaI site. This probe has pBR322 sequences, indicated by wavy line, adjacent to the SalI site of the β-actin gene.

Referring to FIG. 1, as expected, little, if any RNA synthesized from the cDNA version of the gene was detectable in the cytoplasm. On the other hand, RNA synthesized from the genomic version accumulated to high levels. Insertion of sequences from the HSV-TK gene into the 5'-untranslated region of the human β-globin cDNA also enabled high level accumulation of globin-like RNA in the cytoplasm. In sharp contrast to the greater than 100-fold difference in cytoplasmic accumulation observed between cells transfected with pβ1(−)2(−) versus pβ1(+)2(+), only a 2- to 3-fold difference was observed between cells transfected with pTKβ1(−)2(−) versus pTKβ1(+)2(+). Therefore, sequences contained within the transcribed region of the HSV-TK gene can enable efficient processing and cytoplasmic accumulation of intronless chimeric TK-globin RNAs.

4. Localization of an HSV-TK Sequence Element Mediating Intron-independent Gene Expression To look for a positive, cis-acting sequence element in the HSV-TK gene that might enable intron-independent expression of the human β-globin gene, we made a series of TK-deleted variants of pTKβ1(−)2(−) and pTKβ1(+)2(+) (Table 1, below; FIG. 2). FIG. 2 demonstrates that regions of the HSV-TK gene differ in their ability to enable intron-independent expression of the human β-globin gene. Specifically, FIG. 2 is a summary of the structures of plasmids containing different portions of the HSV-TK gene inserted into the NcoI site of the human β-globin gene and the data obtained with these plasmids. The schematic diagrams indicate the regions of the HSV-TK gene inserted into the cDNA and genomic versions of the human β-globin gene as described in Table 1. The symbols are the same as those described in the legend to FIG. 1. Only the TK part of the name of each plasmid is stated.

Still referring to FIG. 2, the column on the right indicates the amount of TK-globin chimeric RNA accumulated in the cytoplasm of cells transfected in parallel with the cDNA versus corresponding genomic version of each pair of plasmids.

Each of these plasmids contains a portion of the transcribed region of the HSV-TK gene inserted at the NcoI site in the 5'-untranslated region of either the cDNA or genomic version of the human β-globin. The relative amounts of the TK-globin chimeric RNAs accumulated in cells transfected with each of these plasmids were determined as described above (summarized in FIG. 2).

Table 1 below summarizes the structures of the TK-globin chimeric genes examined herein.

TABLE 1

| Plasmid[a] | HSV-TK nucleotide residues inserted (altered) into globin NcoI site |
|---|---|
| pβ1(+)2(+)[b] | — |
| pβ1(−)2(−)[c] | — |
| pTKβ1(−)2(−) | 59–1238 |
| pTK583β1(−)2(−) | 170–752 |
| pTK415β1(−)2(−) | 338–752 |
| pTK311β1(−)2(−) | 442–752 |
| pTK142β1(−)2(−) | 338–479 |
| pTK119β1(−)2(−) | 361–479 |

TABLE 1-continued

| Plasmid[a] | HSV-TK nucleotide residues inserted (altered) into globin NcoI site |
|---|---|
| pTK69β1(−)2(−) | 411–479 |
| pTK38β1(−)2(−) | 338–479 (delete 341–444) |
| pTK119ASβ1(−)2(−) | 361–479 antisense |
| pTK119Xβ1(−)2(−) | 361–479 (438 G→A; 433 C→G) |
| p2XTK119β1(−)2(−) | 361–479:361–479 (438 G→A; 433 C→G) |
| pTK119LS0β1(−)2(−) | 361–479 (438 G→A; 433 C→G; 407–419 ATCTACACCACA (SEQ ID NO:4)→ TAGTAGATCTAGA (SEQ ID NO:5) |
| pTK119LS1β1(−)2(−) | 361–479 (438 G→A; 433 C→G; 416–421 ACACAA→AGATCT)[d] |
| pTK119LS2β1(−)2(−) | 361–479 (438 G→A; 433 C→G; 422–427 CACCGC→AGATCT)[d] |

[a]Only the cDNA version of each plasmid is shown; the genomic version of each variant, containing IVS1 and IVS2, was made likewise.
[b]pβ1(+)2(+) is the parental starting plasmid; it contains nucleotide residues −812 through +2156 of the human β-globin gene, including IVS1 and IVS2.
[c]pβ1(−)2(−) is identical to pβ(+)2(+) except for the precise deletion of IVS1 and IVS2.
[d]A unique BglII site (5'-AGATCT-3') was introduced into each plasmid during the mutagenesis.

Different HSV-TK sequences were found to differ significantly in their ability to enable cytoplasmic accumulation of globin-like RNA in the absence of introns. For example, whereas the presence of HSV-TK nt 338-to-752 increased cytoplasmic accumulation of globin-like RNA from intronless transcripts at least 30-fold, the presence of HSV-TK nt 442-to-752 had little effect. Thus, a sequence contained, at least in part, within HSV-TK nt 338-to-442 can provide in cis an element necessary for efficient pre-mRNA processing.

To delineate further the region of the HSV-TK gene that contains this element, we constructed additional plasmids containing insertions of smaller and smaller portions of the nt 338-to-752 region of the HSV-TK gene. Analysis of the globin-like RNAs accumulated in cells transfected with these plasmids indicated that the presence of HSV-TK nt 361-to-479 is sufficient to enable significant cytoplasmic accumulation of globin-like RNA. However, the presence of nt 411-to-479 is not sufficient. Therefore, nt 361-to-479 of the HSV-TK gene contains a positive, cis-acting sequence element that enables intron-independent processing of β-globin transcripts, with at least part of this element being contained within nt 361-to-410. We name sequence elements with this function PPEs for pre-mRNA processing enhancers.

5. HSV-TK PPE Mediates Cytoplasmic Accumulation of β-globin RNA in the Absence of Splicing One trivial possibility is that the TK-globin chimeric RNA accumulated in the cytoplasm of cells transfected with pTK119β1(−)2(−) because the presence of cryptic splice sites enabled splicing to occur despite the absence of known introns. To test this hypothesis, we performed an additional structural analysis of the chimeric RNA accumulated in the cytoplasm using a reverse transcriptase-polymerase chain reaction (RT-PCR) assay with primers corresponding to sequences near the 5'- and 3'-ends of the RNA. All of the TK-globin chimeric RNAs accumulated in cells transfected with the intronless plasmid pTK119β1(−)2(−) were similar in size to the processed TK-globin chimeric RNAs accumulated in cells transfected with the intron-containing plasmid pTK119β1(+)2(+) (data not shown). No bands corresponding to cryptically spliced products were detected. Neither were discontinuities in the RNA detected by S1 nuclease mapping with a probe homologous to pTK119β1(−)2(−) (data not shown). Therefore, we conclude that the PPE contained within nt 361-to-479 of the HSV-TK gene can mediate proper processing and transport of human β-globin-like transcripts in the absence of splicing.

6. HSV-TK PPE Functions in an Orientation-dependent Manner

To determine whether this novel sequence element functions in an orientation-dependent manner, we constructed the plasmids pTK119ASβ1(−)2(−) and pTK119ASβ1(+)2(+) in which HSV-TK nt 361-to-479 were inserted at the NcoI site of the human β-globin gene, but in the anti-sense orientation (FIG. 3). FIG. 3 is a summary of the structures of plasmids containing an insertion of the HSV-TK element in the sense versus anti-sense orientation or in the 5'- versus 3'-UTR of the β-globin gene and the data obtained with these plasmids. The arrows indicate the orientation of the HSV-TK sequences. All other symbols are the same as those described in FIG. 1. The data summarized on the right were obtained as described in FIG. 1.

The data reported in FIG. 3 demonstrated that cells transfected with pTK119β1(−)2(−) efficiently accumulated the chimeric RNA, while cells transfected with pTK119ASβ1(−)2(−) failed to do so. Thus, the orientation of this inserted HSV-TK sequence element is important, consistent with it functioning at the RNA level.

7. Effect of Duplication of this HSV-TK PPE

Although insertion of HSV-TK nt 361-to-479 into the NcoI site of the human β-globin gene leads to fairly efficient rescue of the defects in processing of intronless β-globin-like transcripts, it does not enable cytoplasmic accumulation of globin RNA to the levels obtained when a nearly full-length copy of the transcribed region of the HSV-TK gene is inserted into the β-globin gene (FIGS. 1 and 2). One hypothesis to explain this finding is that more than one PPE is needed for maximally efficient RNA processing. To test this hypothesis, we constructed plasmids p2xTK119β1(−)2(−) and p2xTK119β1(+)2(+) that contain two tandem copies of this 119-bp HSV-TK sequence inserted at the NcoI site of the human β-globin gene. Duplication of this HSV-TK PPE resulted in at least a 2-fold increase in cytoplasmic accumulation of globin-like RNA in the absence of introns (FIG. 4). This level is comparable to the level obtained by insertion of the entire coding region of the HSV-TK gene (FIG. 4 vs. FIG. 1A).

FIG. 4 is a summary of the structures of the plasmids containing tandem copies of HSV-TK nt 361-to-479 and the data obtained with these plasmids. BH indicates BspHI. All other symbols are the same as those described in the legend to FIG. 1. The data summarized on the right were obtained as in FIG. 1.

Greenspan and Weissman (1985, supra) and Buchman and Berg (1988, supra) had noted previously that non-overlapping sequences transcribed from the HSV-TK gene can accumulate in vivo in the absence of intron excision. We now reinterpret this finding to indicate that the HSV-TK transcribed region contains at least two PPEs, rather than no negative, cis-acting element requiring an intron for proper processing and transport. Our finding also demonstrates that two copies of the PPE we have mapped here can function at least additively in permitting intron-independent gene expression.

8. Mutations in this PPE that Affect its Ability to Mediate Intron-independent Gene Expression To identify bases within this 119-bp HSV-TK sequence element required for intron-independent gene expression, we constructed the plasmids pTK119LS0 β1(−)2(−), pTK119LS1β1(−)2(−), and pTK119LS2β1(−)2(−) and their corresponding intron-containing versions. These plasmids are derivatives of pTK119β1(−)2(−) and pTK119β1(+)2(+), respectively, into which linker-scanning substitution mutations had been introduced into the nt 399-to-432 region of the inserted HSV-TK sequence (FIG. 5; Table 1). Note that the nucleotide sequences of the entire 119 bp insert from pTK119LS0, pTK119LS1, and pTK119LS2 are listed as SEQ ID NOs:10, 11 and 12, respectively.

FIG. 5 is a summary of the structures of the plasmids containing linker-scanning mutations in the inserted 119-bp HSV-TK sequence element and the abilities of these variants to enable intron-independent gene expression. The schematic diagrams on the left indicate the sequence of the NruI-to-XhoI region of the 119-bp HSV-TK sequence element present in each plasmid; the underlined, bold-faced letters highlight the altered nucleotides. All other symbols are the same as those described in FIG. 1. The data summarized on the right were obtained as in FIG. 1.

These linker-scanning mutants were found to mediate intron-independent gene expression. Whereas the mutations introduced in pTK119LS0 β1(−)2(−) led to an order-of-magnitude reduction in the cytoplasmic accumulation of the chimeric RNA, those introduced in pTK119LS1β1(−)2(−) and pTK119LS2β1(−)2(−) resulted in a reduction of only 2- to 3-fold. Thus, we conclude that specific bases within nt 399-to-432 of this 119-bp HSV-TK sequence are important for intron-independent expression of the human β-globin gene.

9. A Cellular 68 kDa Protein Specifically Binds to RNA Containing this 119-nt HSV-TK Sequence Pre-mRNAs are usually associated with distinct sets of heterogeneous nuclear ribonucleoproteins (hnRNPs) in the nucleus. To look for nuclear trans-acting factors that bind specifically to RNA corresponding to transcripts of the 119-bp HSV-TK sequence element (i.e., rTK119), we synthesized radiolabeled rTK119 using T7 polymerase and the plasmid pT7/TK119. The labeled transcripts were purified, incubated with extract made from nuclei of HeLa or COS cells, and exposed to UV light to crosslink the bound protein to the radiolabeled RNA. After digestion of the unprotected RNA with RNase A, the RNA-protein adducts were resolved by SDS-PAGE.

Several proteins were found to crosslink with rTK119. However, only the binding of the approximately 68 kDa one was competed in a sequence-specific manner (data not shown). The intensity of the other abundantly crosslinked factor, corresponding to a protein approximately 34 kDa in size, varied between experiments and cell extracts. Quite likely, this latter band corresponds to a proteolytic product of the 68 kDa protein or a non-specific crosslinking product.

10. Binding of this 68 kDa Protein to rTK119 Correlates with the Ability of this PPE to Enable Cytoplasmic Accumulation of mRNA in vivo UV-crosslinking analysis performed with deleted variants of rTK119 indicated that the region of this RNA critical for efficient in vitro binding of the 68 kDa protein is located around nt 387-to-419 (Liu, "Effects of intron and exon sequence elements on intron-dependent and intron-independent gene expression," Ph.D. Thesis. University of Wisconsin-Madison, Madison, Wis., 1994). This same region is also essential for PPE function in vivo (summarized in FIG. 2). To further assess the biological importance of the binding of the 68 kDa protein to rTK119, we examined whether binding of this protein to RNAs containing alterations in this sequence (FIG. 6) correlated with the previously determined abilities of the sequence to enable intron-independent gene expression (FIG. 5).

FIG. 6 is a set of schematic diagrams of the transcribed regions of the plasmids with linker-scanning mutations in the PPE used to synthesize the radiolabeled rTK119, rTK119LS0, rTK119LS1, and rTK119LS2 RNAs and a summary of the UV-crosslinking data obtained with these RNAs. The first column on the right indicates the binding of the 68 kDa protein to each of these RNAs relative to its binding to rTK119 as determined by quantitative analysis with a PhosphorImager of two independent experiments similar to the one shown in panel B. The last column is taken from the data in FIG. 5.

To assay for the abilities of these mutant RNAs to bind the 68 kDa protein, we first constructed the plasmids pT7/TK119LS0, pT7/TK119LS1, and pT7/TK119LS2 (FIG. 6). These plasmids are identical in sequence to pT7/TK119 except for the replacement of the NruI-to-XhoI region with the corresponding region from plasmids pTK119LS0β1(−)2(−), pTK119LS1β1(−)2(−), and pTK119LS2β1(−)2(−) (FIG. 5), respectively. These plasmid DNAs were cleaved with NcoI and transcribed with T7 RNA polymerase in parallel reactions to make rTK119, rTK119LS0, rTK119LS1, and rTK119LS2 radiolabeled to similar specific activities. Identical amounts of each RNA were incubated with equal amounts of HeLa cell nuclear extract and processed as in the UV-crosslinking experiments described above. The relative abilities of these RNAs to bind the 68 kDa protein were determined from the relative intensities of the RNA-protein adducts (data not shown). Quantitative analysis of these data indicated that the efficiencies with which these mutant RNAs bind the 68 kDa protein (FIG. 6) correlate well with their abilities to enable cytoplasmic accumulation of intronless globin-like RNA (FIG. 5).

If sequence-specific binding of the 68 kDa protein to rTK119 is responsible for enabling proper processing and cytoplasmic accumulation of intronless TK119-globin chimeric transcripts, this protein would be expected to bind transcripts synthesized from pTK119β1(−)2(−), but not ones synthesized from pβ1(−)2(−). To test this hypothesis, radiolabeled RNAs corresponding to these transcripts were synthesized with T7 RNA polymerase, incubated with HeLa cell nuclear extract in the presence of the non-specific competitor RNA, pβ19, and exposed to UV-light as described above. Whereas transcripts containing this 119-nt HSV-TK sequence specifically crosslinked with the 68 kDa protein in vitro, the intronless β-globin transcripts did not (data not shown). These data indicate that the pre-mRNAs synthesized from pβ1(−)2(−) and pTK119β1(−)2(−) are differentially bound by the 68 kDa protein, with the presence of the 119-nt HSV-TK sequence being responsible for this difference. Thus, we conclude that binding of this cellular 68 kDa protein to this PPE probably plays an important role in the proper processing and transport of these intronless transcripts. As we show elsewhere (Liu and Mertz, 1995, supra) this 68 kDa protein is hnRNP L, an abundant, cellular protein (Pinol-Roma, et al., *Genes and Devel.* 2:215–227, 1988).

11. The Intronless Cellular Gene c-jun can Also Enable Efficient Accumulation of Intronless β-globin-like RNA Although viral in origin, the HSV-TK PPE identified here is recognized in a sequence-specific manner by hnRNP L, an abundant, 68 kDa cellular protein, and can efficiently perform its function in mammalian cells in the absence of any virally encoded proteins (Liu and Mertz, 1995, supra). Thus, it is likely that at least some cellular genes also contain similar sequence elements. The cellular gene c-jun is naturally intronless, yet efficiently expressed in higher eukaryotes. To test whether this gene might also contain elements functionally similar to the HSV-TK PPE identified here, we inserted part of its coding region (nt 975-to-1963 relative to the transcription initiation site) into the 5'-untranslated region of cDNA and genomic versions of the human β-globin gene.

FIG. 7 is a diagram of structures of the plasmids containing an insertion of part of the coding region of the c-jun gene into the 5'-untranslated region of the human β-globin gene and a summary of the data obtained with them. Only the transcribed region of each gene is shown. Stippled rectangles indicate sequences from the transcribed region of the c-jun gene; numbers at ends of stippled rectangles indicate endpoints of the c-jun sequence inserted in nt relative to the c-jun gene's transcription initiation site. All other symbols are as described in the legend to FIG. 1.

Analysis of the jun-globin hybrid RNA accumulated in CV-1PD cells transfected with these chimeric genes indicated that sequence from c-jun can also enable intron-independent processing and/or transport of β-globin-like RNA (summarized in FIG. 7). Therefore, the transcribed region of the cellular gene c-jun probably also contains at least one sequence element functionally similar to the HSV-TK PPE.

a. Role of HSV-TK PPE in Intron-independent Gene Expression

Much evidence indicates that the requirement of introns for the efficient expression of intron-dependent genes is post-transcriptional in nature (Gruss, et al., 1979, supra; Hamer and Leder, 1979, supra; Buchman and Berg, 1988, supra; Ryu and Mertz, 1989, supra; Collis, et al., 1990, supra; Huang and Gorman, 1990, supra; Nesic, et al., 1993, supra). The HSV-TK PPE identified here probably also acts post-transcriptionally. First, the presence of this element in an intron-containing gene has little effect on cytoplasmic accumulation of the resulting mRNA. Second, the functioning of this element is orientation dependent. Third, transcripts containing this sequence specifically interact with a 68 kDa protein present in nuclear extracts (FIG. 6). Fourth, a good correlation exists between binding of this 68 kDa protein, hnRNP L, to this RNA element and its ability to function in vivo (FIG. 6) (Liu and Mertz, 1995, supra). Thus, although we have not yet definitively eliminated the possibility that this element acts in transcription, a post-transcriptional mechanism is much more likely.

Transcripts synthesized from intronless variants of intron-requiring genes are retained in the nucleus where they are degraded (FIG. 1; Ryu and Mertz, 1989, supra; Collis, et al., 1990, supra; Huang and Gorman, 1990, supra, and references cited therein). One hypothesis to explain nuclear retention is that specific sequence elements present in transcripts prevent nucleocytoplasmic transport by binding proteins restricted to the nucleus. One such cis-acting sequence element other than splicing signals that is responsible for nuclear retention of pre-mRNAs has been identified in HIV; Brighty and Rosenberg, *Proc. Natl. Acad. Sci. USA* 91:8314–8318, 1994). Nuclear retention can then be overcome by the interactions of trans-acting factors that enable nuclear export (e.g., the HIV-encoded protein rev) with specific cis-acting sequences present in these transcripts (e.g., RRE). Therefore, specific RNA sequence elements exist that can either positively or negatively regulate nuclear export of mRNAs.

In the presence of the HSV-TK PPE, intronless globin-like transcripts are both stabilized in the nucleus and exported to the cytoplasm (FIG. 1B; Ryu, 1989, supra). However, stabilization of RNA in the nucleus need not imply nucleocytoplasmic transport. For example, unspliced HIV transcripts are stabilized, yet restricted to the nuclei of COS cells in the absence of rev (Cullen, et al., 1988, supra; Emerman, et al., 1989, supra; Felber, et al., 1989, supra; Hammarskjold, et al., 1989, supra; Malim, et al., 1989, supra). In human T cells, these same transcripts are degraded (Malim and Cullen, *Mol. Cell. Biol.* 13:6180–6189, 1993). The presence of rev not only enables the nucleocytoplasmic transport of unspliced viral mRNAs, but also acts to stabilize these mRNAs in T cell nuclei.

The mechanism of nuclear stabilization remains unclear. Lu, et al. (1990, supra) have shown that the presence of the tat/rev 5' splice site is essential for the nuclear stability of unspliced transcripts of HIV. We have noted that nts 435–443 (AGG/GUGAGA) of the HSV-TK PPE share significant homology to the 5' splice site consensus sequence. However, (i) a nt 438 (GT-AT) point mutation, predicted to inactive this putative splice site-like sequence, does not affect its function, and (ii) transcripts synthesized from pTK69 β1(–)2(–) contain this sequence, yet fail to accumulate in the cytoplasm. Therefore, this HSV-TK PPE functions independently of this putative 5' splice sequence. Thus, we conclude that interaction of this HSV-TK PPE sequence with hnRNP L is probably responsible for nuclear stabilization of the intronless TK-globin transcripts.

One plausible hypothesis is that stabilization and nuclear export are consequences of proper 3'-end formation. The presence of introns has been shown to stimulate cleavage and polyadenylation of many pre-mRNAs in vitro (Niwa, et al., 1990, supra; Niwa and Berget, *Genes & Dev.* 5:2086–2095, 1991) and in vivo (Collis, et al., 1990, supra; Pandey, et al., 1990, supra; Chiou, et al., *J. Virol.* 65:6677–85, 1991; Nesic, et al., 1993, supra; Liu, 1994, supra; Nesic and Maquat, *Genes & Dev.* 8:363–375, 1994). Transport of intronless histone transcripts is stimulated by proper 3'-end formation (Eckner, et al., *EMBO. J.* 10:3513–3522, 1991). We find that the presence of this HSV-TK PPE in intronless β-globin transcripts leads to an increase in the accumulation of polyadenylated β-globin-like RNA (unpublished observation). Thus, this HSV-TK PPE might function primarily to facilitate 3'-end formation. However, our finding that it functions well in the 5'-UTR, but not when inserted close (e.g., 21 bases) to the polyadenylation signal (data not shown), does not support this simple model.

b. RNA-protein Interactions in Pre-mRNA Processing

Nascent transcripts rapidly associate with hnRNP proteins and snRNPs in a sequence-specific manner (Bennett, et al., *Mol. Cell. Biol.* 12:3165–3175, 1992; Dreyfuss, et al., *Rev. Biochem.* 62:289–321, 1993; Matunis, et al., *J. Cell. Biol.* 121:219–228, 1993). The specific arrangement of hnRNPs on a transcript is likely an important determinant of the subsequent steps in mRNA biogenesis and transport. For example, Swanson and Dreyfuss (1988, supra) have shown that the major hnRNP proteins A1, C, and D specifically bind to the 3'-ends of the introns of human β-globin pre-mRNA; however, no specific, high-affinity binding sites for these proteins exist on intronless globin RNAs. Using a UV-crosslinking assay, we observed only one significant difference in the pattern of proteins bound to the intronless β-globin transcripts containing the 119-nt HSV-TK sequence versus ones lacking it, i.e., the presence of a band corresponding to a protein 68 kDa in size (data not shown). Immunoprecipitation with an anti-hnRNP L-specific serum and direct UV-crosslinking experiments with recombinant hnRNP L indicated that the 68 kDa protein is hnRNP L (data not shown). Binding of hnRNP L to the transcript was found to correlate with efficient processing and transport of the RNA (data not shown). Thus, we conclude that the binding of hnRNP L probably plays an important role in the proper processing and transport of intronless human β-globin mRNA containing this HSV-TK PPE.

Several hnRNP proteins have been shown to bind RNA in a sequence-specific manner. For example, hnRNP A1 binds to 5' splice site-like sequences (Burd and Dreyfuss, *EMBO. J.* 13:1197–204, 1994), hnRNP I binds to polypyrimidine tract sequences (Garcia-Blanco, et al., *Genes & Dev.* 3:1874–1886, 1989; Patton, et al., *Genes & Dev.* 5:1237–51, 1991; Bennett, et al., 1992, supra; Ghetti, et al., *Nucleic Acids Res.* 20:3671–8, 1992), and hnRNP K has a high affinity for poly(C)-rich sequences (Swanson and Dreyfuss, *Mol. Cell. Biol.* 8:2237–2241, 1988; Matunis, et al., 1992, supra). Specific RNA-protein interactions often regulate important steps in pre-mRNA processing. By mutational analysis, we showed here that hnRNP L binds to RNA with high sequence specificity. HnRNP L is an abundant, nuclear protein found in association with some of the nascent transcripts observed in the giant loops of lampbrush chromosomes of amphibian oocytes (Pinol-Roma, et al., *J. Cell. Biol.* 109:2575–2587, 1989). At least some of the hnRNP L present in cells exists free from association with previously defined hnRNP complexes (Pinol-Roma, et al., 1989, supra). The precise function of hnRNP L is not yet known. One possibility is that hnRNP L functions to shuttle between the nucleus and cytoplasm RNAs to which it is bound, much like hnRNP A1 has been shown to do (Pinol-Roma and Dreyfuss, *Nature* 355:730–732, 1992). A second possibility is that binding of this protein in the 5'-UTR helps to insure the rapid formation of ribonucleoprotein complexes on the nascent transcripts, thereby protecting the RNAs from degradation in the nucleus and, consequently, allowing the RNAs to be efficiently processed and, eventually, exported to the cytoplasm. A third, and not mutually exclusive, possibility is that binding of hnRNP L may facilitate recruitment to the RNA of other hnRNP proteins that, subsequently, function in other steps in pre-mRNA processing (e.g., polyadenylation) and transport to the cytoplasm.

We claim:

1. A chimeric RNA molecule comprising a 5' untranslated region, a 3' untranslated region and a protein-coding sequence, wherein the 5' untranslated region or the 3' untranslated region of the RNA molecule comprises at least one pre-mRNA processing element not natively connected to the protein-coding sequence, wherein the pre-mRNA processing enhancer has a nucleotide sequence selected from the group consisting of SEQ ID NO:1, NO:11, and NO:12.

2. A gene construct comprising a DNA sequence encoding at least one pre-mRNA processing enhancer downstream from a promoter and upstream from a protein coding sequence, wherein the promoter is operably connected to the protein-coding sequence, wherein the pre-mRNA processing enhancer is not natively connected to the protein coding sequence and wherein the pre-mRNA processing enhancer increases the accumulation of the protein coding sequence at least two-fold without requiring intron excision and wherein a single pre-mRNA processing enhancer is localized to a nucleotide length of less than 300 nucleotides.

3. A chimeric RNA molecule comprising a 5' untranslated region, a 3' untranslated region and a protein-coding sequence, wherein the 5' untranslated region of the RNA molecule comprises at least one pre-mRNA processing element not natively connected to the protein-coding sequence and wherein the pre-mRNA processing enhancer is within the 5' untranslated region, additionally comprising a translation enhancer sequence upstream from the protein-coding sequence and downstream from the pre-mRNA processing enhancer.

4. A gene construct comprising a DNA sequence encoding at least one pre-mRNA processing enhancer, wherein said construct comprises a unique restriction endonuclease site downstream from said DNA sequence and wherein the restriction endonuclease site is part of a polylinker.

\* \* \* \* \*

UNITED STATES PATENT AND TRADEMARK OFFICE
CERTIFICATE OF CORRECTION

PATENT NO. : 5,686,120

DATED : November 11, 1997

INVENTOR(S) : Janet E. Mertz and Xuedong Liu

It is certified that error appears in the above-identified patent and that said Letters Patent is hereby corrected as shown below:

Column 1, line 1,

--This invention was made with United States government support awarded by NIH GRANT NOS. CA-22443 and CA-07175. The United States Government has certain rights in this invention.--

Title pages, item [56]   OTHER PUBLICATIONS

"Huang and Gorman, . . . sequeces . . ."
               s/b
--Huang and Gorman, . . . sequences . . .--

"Legrain, P., et al., . . . "Come . . ."
                    s/b
--Legrain, P., et al., . . . Some . . .--

Column 6, line 2

"protein- encoding" s/b --protein-encoding--

Column 19, line 19

"(GT-AT)" s/b --(GT→AT)--

Signed and Sealed this

Tenth Day of November 1998

*Attest:*

BRUCE LEHMAN

*Attesting Officer*   *Commissioner of Patents and Trademarks*